United States Patent
Zabudkin et al.

(10) Patent No.: US 8,846,882 B2
(45) Date of Patent: Sep. 30, 2014

(54) METHOD OF PRODUCING 4-DEMETHOXYDAUNORUBICIN

(75) Inventors: Alexander Zabudkin, Donetsk (UA); Victor Matvienko, Donetsk (UA); Alexey Matvyeyev, Donetsk (UA)

(73) Assignee: Synbias Pharma AG (CH)

( * ) Notice: Subject to any disclaimer, the term of this patent is extended or adjusted under 35 U.S.C. 154(b) by 706 days.

(21) Appl. No.: 13/097,131

(22) Filed: Apr. 29, 2011

(65) Prior Publication Data
US 2012/0277415 A1   Nov. 1, 2012

(51) Int. Cl.
C07H 15/252    (2006.01)

(52) U.S. Cl.
CPC .................................... *C07H 15/252* (2013.01)
USPC .......................................................... 536/6.4

(58) Field of Classification Search
USPC ........................................................ 536/6.4
See application file for complete search history.

(56) References Cited

U.S. PATENT DOCUMENTS

| | | | |
|---|---|---|---|
| 3,963,760 A | 6/1976 | Bernardi et al. | |
| 4,012,284 A | 3/1977 | Di Marco et al. | |
| 4,154,745 A | 5/1979 | Kende et al. | |
| 4,161,480 A | 7/1979 | Pappo et al. | |
| 4,188,377 A | 2/1980 | Suarato et al. | |
| 4,298,535 A | 11/1981 | Vogel et al. | |
| 4,448,724 A | 5/1984 | Cava et al. | |
| 4,471,052 A | 9/1984 | Mitscher et al. | |
| 4,489,206 A | 12/1984 | Cava et al. | |
| 4,496,485 A | 1/1985 | Garland | |
| 4,564,674 A | 1/1986 | Terashima et al. | |
| 4,697,005 A | 9/1987 | Swenton et al. | |
| 4,973,674 A | 11/1990 | Brasca et al. | |
| 4,985,548 A | 1/1991 | Caruso et al. | |
| 5,103,029 A | 4/1992 | Cabri et al. | |
| 5,162,512 A | 11/1992 | King et al. | |
| 5,180,758 A | 1/1993 | Cabri et al. | |
| 5,218,130 A | 6/1993 | Cabri et al. | |
| 5,510,469 A | 4/1996 | Faiardi et al. | |
| 5,587,495 A | 12/1996 | Cabri | |
| 5,731,313 A | 3/1998 | Suarato et al. | |
| 5,776,458 A | 7/1998 | Angelucci et al. | |
| 5,874,412 A | 2/1999 | Priebe et al. | |
| 5,945,518 A | 8/1999 | Bigatti et al. | |
| 5,985,887 A | 11/1999 | Caruso et al. | |
| 5,998,615 A | 12/1999 | Suarato et al. | |
| 6,096,888 A | 8/2000 | Suarato et al. | |
| 6,194,422 B1 | 2/2001 | Caruso et al. | |
| 6,218,519 B1 | 4/2001 | Kenten et al. | |
| 6,512,101 B1 | 1/2003 | King et al. | |
| 7,053,191 B2 * | 5/2006 | Zabudkin et al. | 536/6.4 |
| 7,388,083 B2 * | 6/2008 | Matvienko et al. | 536/6.4 |
| 8,357,785 B2 | 1/2013 | Zabudkin | |
| 2004/0236086 A1 | 11/2004 | Zabudkin et al. | |
| 2007/0135624 A1 * | 6/2007 | Zabudkin et al. | 536/6.4 |
| 2009/0176974 A1 * | 7/2009 | Zabudkin et al. | 536/6.4 |

FOREIGN PATENT DOCUMENTS

| | | |
|---|---|---|
| EP | 04/36474 A1 | 7/1991 |
| EP | 03/28399 B1 | 8/1993 |
| WO | WO-01/25179 A1 | 4/2001 |
| WO | WO-01/87814 A2 | 11/2001 |

OTHER PUBLICATIONS

Pearson, Journal of Chemical Education, 1968, 45(9), 581-87.*
"European Application No. 12 160 375.7, Communication Pursuant to Article 94(3) EPC dated May 7, 2013", (May 7, 2013), 4 pgs.
"European Application No. 12 160 375.7, Communication Pursuant to Article 94(3) EPC dated Jan. 15, 2013", 5 pgs.
"European Application No. 12160375.7, European Search Report dated Jun. 4, 2012", 6 pgs.
"European Application No. 12 160 375.7, Communication Under Rule 71(3)—Intention to Grant, mailed Oct. 14, 2013", 33 pgs.

* cited by examiner

*Primary Examiner* — Ganapathy Krishnan
(74) *Attorney, Agent, or Firm* — Schwegman Lundberg & Woessner, P.A.

(57) ABSTRACT

The present invention relates to a method for the synthesis of 4-demethoxydaunorubicin (idarubicin) having the chemical structure of formula (I), which involves the demethylation of 3'-Prot-daunorubicin in the presence of a soft Lewis acid. The method of the present invention does not comprise cleavage of the glycosidic linkage at carbon C7, thus resulting in a faster synthesis cycle and an improved yield of the final product.

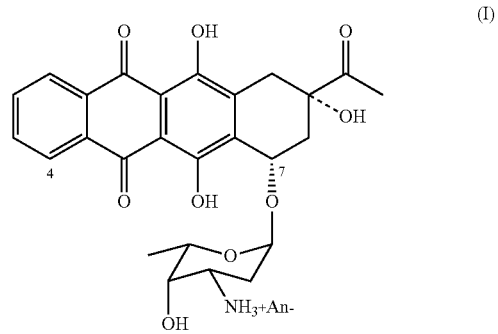

(I)

8 Claims, No Drawings

METHOD OF PRODUCING 4-DEMETHOXYDAUNORUBICIN

FIELD OF THE INVENTION

The present invention relates to methods for the chemical synthesis of anthracycline compounds. More particularly, the invention is directed to a method for the production of 4-demethoxydaunorubicin (idarubicin), starting from daunorubicin.

BACKGROUND OF THE INVENTION

Anthracyclines represent a class of naturally occurring bioactive compounds derived from bacteria of the genus *Streptomyces*. Several anthracyclines were clinically demonstrated to be effective anti-neoplastic agents that can be employed for the treatment of a wide range of cancers including inter alia breast cancer, ovarian cancer, lung cancer, and hematological malignancies such as leukemias and lymphomas. In addition, members of this class of compounds were also shown to be useful in bone marrow transplants and during stem cell transplantation. Examples of such therapeutically relevant anthracyclines include inter alia daunorubicin, idarubicin (i.e. 4-demethoxydaunorubicin), doxorubicin, epirubicin, pirarubicin, zorubicin, aclarubicin, and caminomycin.

4-Demethoxydaunorubicin (idarubicin) having the chemical structure of formula (I) (cf. below) is an analog of daunorubicin that interferes with nucleic acid synthesis by intercalating into DNA and interacts with the enzyme topoisomerase II. The absence of a methoxy group at position 4 of the anthracycline structure gives the compound a high lipophilicity, which results in an increased rate of cellular uptake compared with other anthracyclines. In combination with cytosine arabinoside 4-demethoxydaunorubicine is the current first line therapy of acute myeloid leukemia.

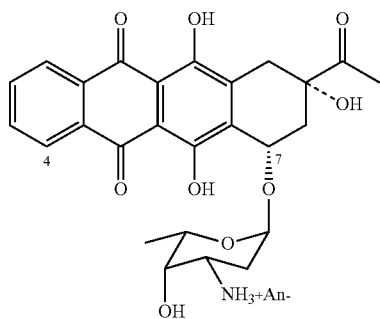

(I)

wherein An⁻ represents an anion such as chloride.

Available methods for the chemical synthesis of 4-demethoxydaunorubicin (idarubicin) are generally based on the coupling of the aglycone of the compound (i.e. the non-sugar component) and the protected and activated daunosamine (i.e. 3-amino-2,3,6-trideoxy-L-lyxo-hexose; the sugar component) in the presence of silver triflate ($AgOSO_2CF_3$), trimethylsilyl-triflate (($CH_3$)$_3SiOSO_2CF_3$), or a mercuric oxide-mercuric bromide system (HgO—$HgBr_2$). The aglycone may, for example, be synthesized using either anthracenetetrone or isobenzofurane as starting material. However, such synthesis methods are complex due to the creation of optically active centers at carbons C7 and C9.

Alternative methods for the synthesis of 4-demethoxydaunorubicin utilize the aglycone of daunorubicin, which is prepared by the acidic hydrolysis of daunorubicin. In case, daunorubicin is subjected to acid degradation, the amino sugar daunosamin can be obtained separately, which is subsequently used, after chemical modification, for the glycosylation of the modified aglycone.

The first methods available for replacing the 4-$CH_3O$ (4-MeO) aglycone group for hydrogen (and other substituents such as $NH_2$) involved demethylation of daunorubicinone, sulfonation of the resulting 4-demethyldaunorubicinone, and substitution of the 4-$ArSO_2O$ group for 4-$ArCH_2NH$, followed by further reduction of the benzyl group to produce the 4-$NH_2$ group (cf. U.S. Pat. No. 4,985,548). Performing a subsequent reductive deamination step results in the production of the aglycone of 4-demethoxydaunorubicin (cf. EP Patent No. 0328399 B1).

U.S. Pat. No. 5,587,495 discloses a reductive condensation reaction of 4-demethyl-4-trifluoromethanesulfonyl daunorubicinone (4-OTf daunorubicinone) and phenylphosphine/palladium or nickel complexes. Concomitantly, 4-R substituted daunorubicinones are obtained.

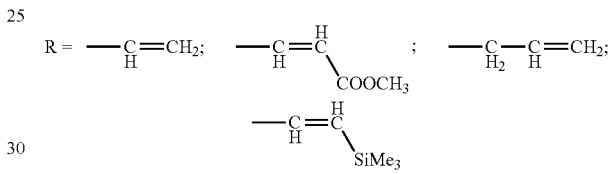

In a similar manner, the reductive carbonylation of 4-OTf daunorubicinone using the same complexes yields 4-COOR substituted daunorubicinones (cf. U.S. Pat. No. 5,218,130). If formate is used as reducing agent, the 4-OTf radical is replaced for hydrogen resulting in the production of 4-demethoxydaunorubicinone (cf. U.S. Pat. No. 5,103,029).

Hence, the established synthesis methods of 4-demethoxydaunorubicine all involve the fragmentation of the daunorubicin molecule in the aglycone component and the amino sugar component, separate chemical modification of the two components, and subsequent coupling. However, such synthesis scheme gives rise to an additional task, the generation of an optically active center at carbon C7. Typically, such synthesis schemes involve 10 to 12 different steps, thus reducing the overall yield of the final product to 6-8%.

U.S. Pat. No. 7,053,191 discloses an alternative synthesis route, in which derivatives of 4-demethyldaunorubicin (i.e. caminomycin), primarily N-trifluoroacetyl-4-demethyldaunorubicin were used as a starting compound. In this case, 4-OH group is removed from the full anthracycline molecule. To date, however, N-trifluoroacetyl-4-demethyldaunorubicin can only be obtained in reasonable amounts by means of complex chemical synthesis (cf. U.S. Pat. No. 4,188,377).

The advantageous modification of the synthesis route for caminomycin derivatives could be seen in the use of daunorubicin as starting material in order to reduce the number of synthesis steps required. However, so far it has not been possible to establish such synthesis scheme due to the lack of methods for the selective demethylation of the 4-MeO group of anthracyclines without concomitant cleavage of the glycosidic linkage at carbon C7.

One established method for demethylation of alkylphenyl ethers comprises the treatment of the alkylphenyl ethers with the strong Lewis acid $AlCl_3$ in inert solvents (in particular, chlorinated hydrocarbons such as dichloromethane) at boiling point. Any attempt to apply this synthesis route to daunorubicin results in the removal of daunosamine followed by total destruction of the molecule.

Thus, there is still a need for new synthesis routes for the production of clinically efficient anthracycline compounds such as 4-demethoxydaunorubicine (idarubicin). In particular, there remains a need for less complex synthesis schemes involving a reduced number of reaction steps and thus resulting in an improved yield of the final product.

Accordingly, it is an object of the present invention to provide such methods.

SUMMARY OF THE INVENTION

In one aspect, the present invention relates to a method for the production of 4-demethoxydaunorubicin or a salt thereof having the chemical structure of formula (I),

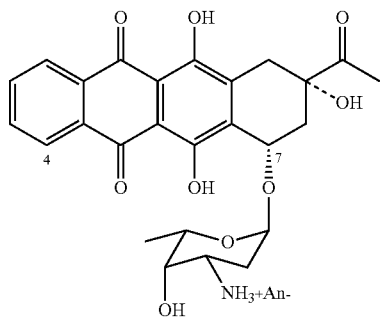

(I)

wherein An— represents an anion; comprising:

(a) converting a daunorubicin salt having the chemical structure of formula (II)

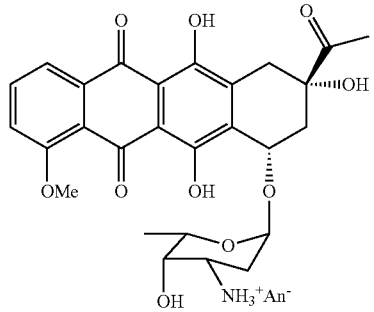

(II)

wherein An— is an independently selected anion, into a 3'-protected daunorubicin (3'-Prot-daunorubicin) being selected from the group consisting of the compounds having the chemical structures of formulas (III) and (IV), wherein conversion of the 3'-amino group salt to a 3'-azide by contacting with an azide-forming reagent results in formation of (III), and conversion of the 3'-amino group to a 3'-trifluoroacetmide by contacting with a trifluoroacetylating reagent results in formation of (IV);

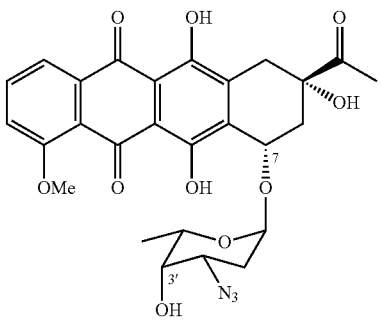

(III)

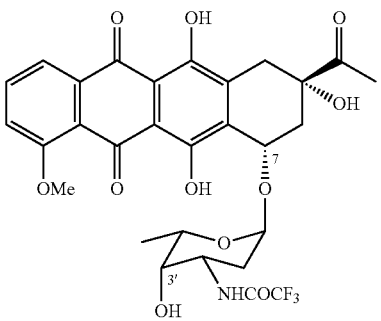

(IV)

(b) demethylating the 3'-Prot-daunorubicin of formula (III) or (IV) by contacting with a soft Lewis acid in an anhydrous solvent to yield a 4-demethyl-3'-Prot-daunorubicin being selected from the group consisting of the compounds having the chemical structures of formulas (V) and (VI) respectively, wherein demethylation of (III) results in formation of (V), and demethylation of (IV) results in formation of (VI);

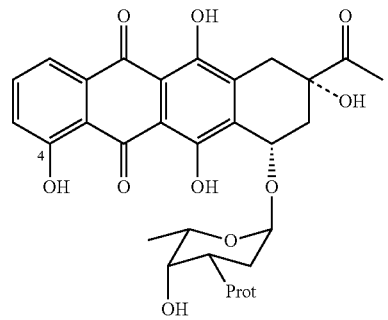

Prot = $N_3$ (V)
Prot = $NHCOCF_3$ (VI)

(c) trifluoromethanesulfonating the 4-demethyl-3'-Prot-daunorubicin of formula (V) or (VI) by contacting with a trifluoromethanesulfonation reagent to yield a 4-O-trifluoromethanesulfonyl-3'-Prot-daunorubicin being selected from the group consisting of the compounds having the chemical structures of formulas (VII) and (VIII), wherein trifluoromethanesulfonation of (V) results in formation of (VII), and trifluoromethanesulfonation of (VI) results in formation of (VIII);

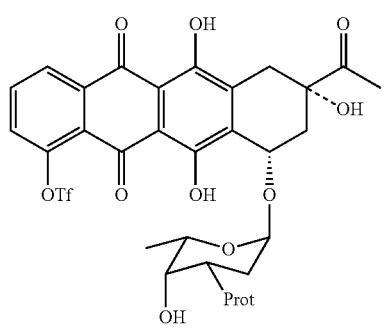

4-Tf-3'-Prot
Daunorubicine

Prot = N$_3$ (VII)
Prot = NHCOCF$_3$ (VIII)

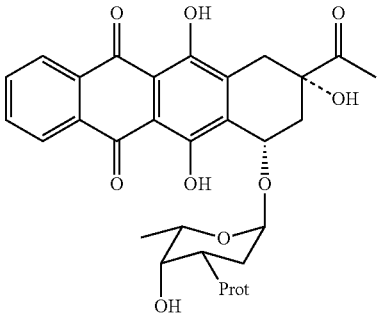

3'-Prot-4-demethoxy
daunorubicine

Prot = N$_3$ (IX)
Prot = NHCOCF$_3$ (X)

(d) reducing the 4-O-trifluoromethanesulfonyl-3'-Prot-daunorubicin by contacting with a reducing agent to yield a 4-demethoxy-3'-Prot-daunorubicin being selected from the group consisting of the compounds having the chemical structures of formulas (IX) and (X), wherein reduction of (VII) results in formation of (IX), and reduction of (VIII) results in formation of (X); and (e) removing the protective 3'-Prot group from the 4-demethoxy-3'-Prot-daunorubicin selected from the group consisting of compound of formula (IX) and the compound of formula (X), wherein the compound of formula (IX) is contacted with an azide-reducing reagent, or the compound of formula (X) is contacted with an alkaline solution, with resulting formation of a 3'-amino group, to yield 4-demethoxydaunorubicin and, optionally, contacting 4-demethoxydaunorubicin with an acid of formula H$^+$An$^-$ to yield 4-demethoxydaunorubicin salt of formula (I).

The method of the present invention does not cause cleavage of the glycosidic linkage at carbon C7, thus enabling the person of ordinary skill to obtain the product in only five chemical steps with an overall yield of the final product of 30-45% from daunorubicin hydrochloride.

The following schematic illustration (Scheme 1) depicts the synthesis route according to the method of the present invention.

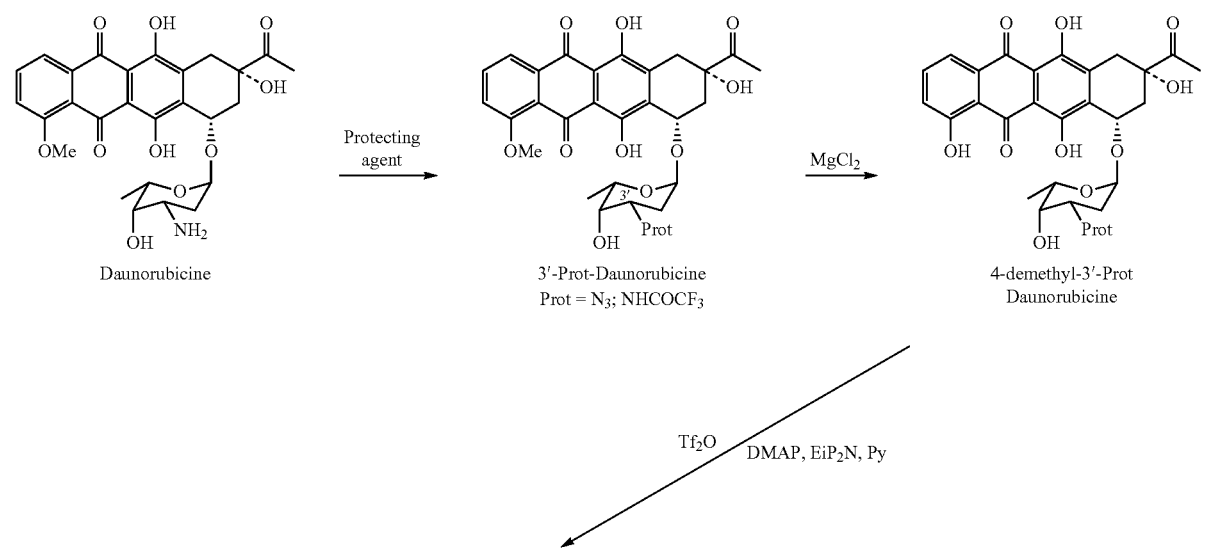

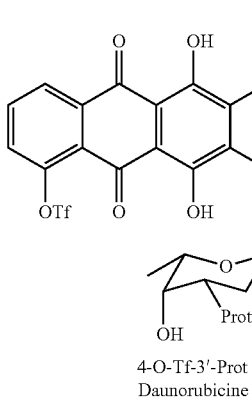

4-O-Tf-3'-Prot
Daunorubicine

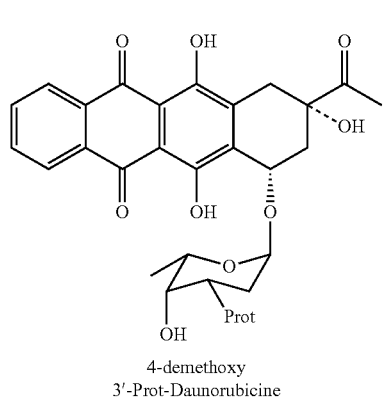

4-demethoxy
3'-Prot-Daunorubicine

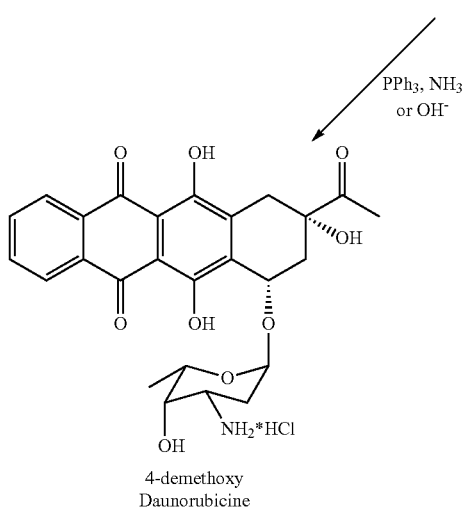

4-demethoxy
Daunorubicine

A daunorubicin salt such as the hydrochloride salt, having the chemical structure of formula (II), is protected at the 3'-amino group (of the aminosugar moiety) which, in a first step, is converted into an azide (3'-$N_3$) (cf. the compound having the chemical structure of formula (III)) or to a trifluoroacetamide (3'—$NHCOCF_3$) (cf. the compound having the chemical structure of formula (IV)). The first alternative transformation can be carried out by contacting the compound of formula (II) with an azide-forming reagent. An example is sodium nitrite/sodium azide. A preferred example is trifluoromethanesulfonyl azide (Tf$N_3$). The second alternative transformation can be carried out by contacting the compound of formula (II) with a trifluoroacetylating reagent, such as trifluoroacetic anhydride, or an activated ester of trifluoroacetic acid, such as the N-hydroxysuccinimide ester.

Then, the 3'-Prot-daunorubicin of formula (III) or (IV) thus obtained can be O-demethylated at the 4-position in the presence of a soft Lewis acid, preferably $MgCl_2$ (anhydrous). In particular embodiments, this step is performed at a reaction temperature in the range of 10-80° C., preferably in the range of 40-60° C. In further particular embodiments, the reaction takes place in the presence of KI in an anhydrous solvent being selected from the group consisting of alkanes, cycloalkanes, halogenalkanes, arenes, alkyl oxides, ethers, $C_4$-$C_6$ alcohols, and carbon disulfide. This step results in the demethylation of 4-OMe group without cleavage of the glycosidic linkage at carbon C7. Improved yields are obtained with an azide protecting group at the 3'-position.

The 4-demethyl-3'-Prot-daunorubicin of formula (V) or (VI) thus obtained can then be trifluoromethanesulfonated by contacting with a trifluoromethanesulfonation reagent to yield a 4-O-trifluoromethanesulfonyl-3'-Prot-daunorubicin of formulas (VII) or (VIII) respectively. Then, the compound of formula (VII) or of formula (VIII) can be reduced to yield a 4-demethoxy-3'-Prot-daunorubicin of formulas (IX) and (X) respectively. The trifluoromethanesulfonation reaction can be performed by reacting the 4-demethyl-3'-Prot-daunorubicin of formula (V) or (VI) with trifluoromethanesulfonic anhydride, preferably in pyridine in the presence of tertiary amines.

In particular embodiments, the reduction step of the compound of formula (VII) or (VIII) to yield the compound of formula (IX) or (X) respectively is performed with a reducing agent in the presence of catalytic amounts of compounds having the general formula $PdL_nL'_m$; wherein Pd represents palladium, L and L' are independently selected from the group consisting of phosphites and phosphines; and n and m may independently vary from 0 to 4. Preferably, the reducing agent is selected from the group consisting of formic acid and salts of formic acid. In further preferred embodiments, the reduction step is performed at a reaction temperature in the range of 30-100° C. in a polar aprotic solvent.

In specific embodiments, the method of the present invention further comprises isolating the 4-demethoxy-3'-Prot-daunorubicin obtained by treatment of the reaction mixture with strong acids at a pH of 2.5±1.0 and subsequent extraction (with water-insoluble organic solvents including inter alia halogenalkanes, cycloalkanes, arenes, $C_4$-$C_6$ alcohols as well as mixtures thereof). The 4-demethoxy-3'-Prot-daunorubicin compound is isolated by evaporation of the organic phase in vacuum.

The final removal of the protective 3'-Prot group from the 4-demethoxy-3'-Prot-daunorubicin is performed by using the methods described in the prior art (cf. the references referred to above) for modification of the aglycone 4-demethyl-daunomycinone. The reduction of the 3'-N$_3$ group with regeneration of 3'—NH$_2$ can be performed in the presence of triphenylphosphine (PPH$_3$)—NH$_3$, whereas removal of the COCF$_3$ protecting group is accomplished by alkaline hydrolysis of the amide.

In a further aspect, the present invention relates to a method for producing and isolating a key intermediate 4-demethyl-3'-Prot-daunorubicine, of formulas (V) or (VI), starting from daunorubicin hydrochloride, by performing the reaction steps as described above. These protected caminomycin derivatives can be converted to caminomycin using the deprotection procedures described for deprotection of the protected 4-demethoxydaunorubicin (idarubicin) compounds above, to provide caminomycin or a salt thereof.

DETAILED DESCRIPTION OF THE INVENTION

The present invention is related to the unexpected finding that demethylation of 3'-Prot-daunorubicin in the presence of a soft Lewis acid, preferably MgCl$_2$ (anhydrous), enables the synthesis of 4-demethoxydaunorubicine from daunorubicin hydrochloride without cleavage of the glycosidic linkage at carbon C7, thus resulting in a faster synthesis cycle and an improved yield of the final product.

The present invention will be described in the following with respect to particular embodiments and with reference to certain drawings but the invention is to be understood as not limited thereto but only by the appended claims. The drawings described are only schematic and are to be considered non-limiting.

Where the term "comprising" is used in the present description and claims, it does not exclude other elements or steps. For the purposes of the present invention, the term "consisting of" is considered to be a preferred embodiment of the term "comprising". If hereinafter a group is defined to comprise at least a certain number of embodiments, this is also to be understood to disclose a group, which preferably consists only of these embodiments.

Where an indefinite or definite article is used when referring to a singular noun e.g. "a", "an" or "the", this includes a plural of that noun unless specifically stated otherwise.

In case, numerical values are indicated in the context of the present invention the skilled person will understand that the technical effect of the feature in question is ensured within an interval of accuracy, which typically encompasses a deviation of the numerical value given of ±10%, and preferably of ±5%.

Furthermore, the terms first, second, third, (a), (b), (c), and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Further definitions of term will be given in the following in the context of which the terms are used. The following terms or definitions are provided solely to aid in the understanding of the invention. These definitions should not be construed to have a scope less than understood by a person of ordinary skill in the art. In a first step, the 3'-amino group of daunorubicin is protected, either as an azido group or as a trifluoroacetamide.

In some embodiments, the conversion of 3'-amino group of daunorubicin hydrochloride into 3-azido compound (3'-N$_3$) can be performed by using an azide-forming reagent, such as trifluoromethanesulfonyl azide (TfN$_3$) in accordance with the following scheme 2:

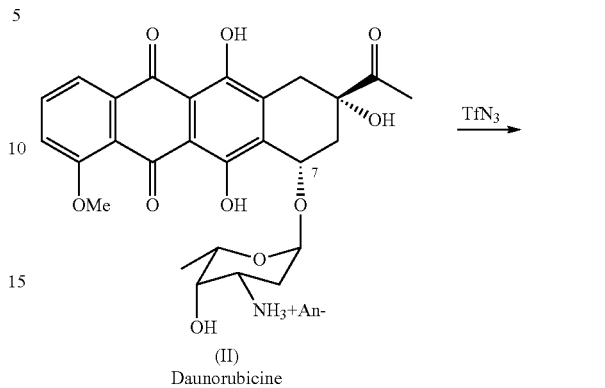

(II)
Daunorubicine

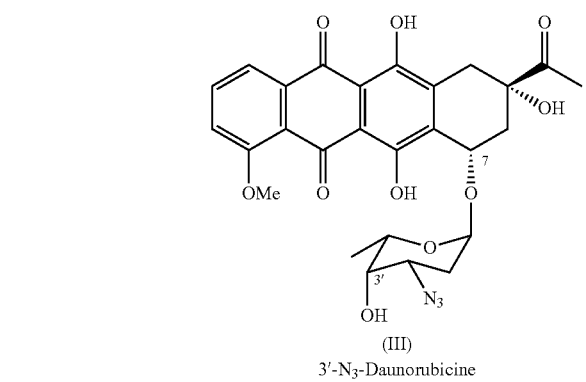

(III)
3'-N$_3$-Daunorubicine

In alternative embodiments, the protection of the 3'-amino group of daunorubicin hydrochloride can be achieved by use of the corresponding 3'-trifluoroacetamide (3'—NHCOCF$_3$), which can be prepared by contacting the 3-amino compound (II) and trifluoroacetic anhydride in accordance with the following scheme 3:

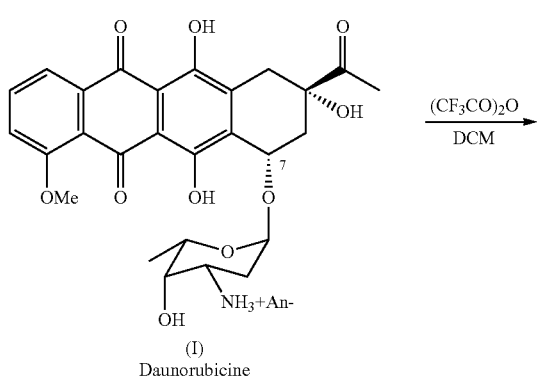

(I)
Daunorubicine

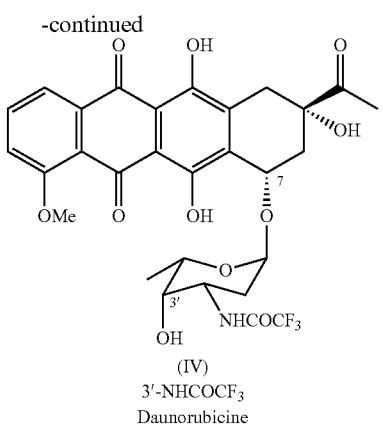

(IV)
3'-NHCOCF₃
Daunorubicine

The step of demethylation of 4-OMe group of the 3'-Prot-daunorubicine of formulas (III) or (IV) can be performed by contacting the compound of formula (III) or (IV) with a Lewis acid, in particular with a soft Lewis acid such as anhydrous MgCl₂, to provide the phenolic intermediates, caminomycin derivatives (V) or (VI) respectively (see Scheme 4, below).

The following scheme 4 illustrates the 4-demethylation reaction:

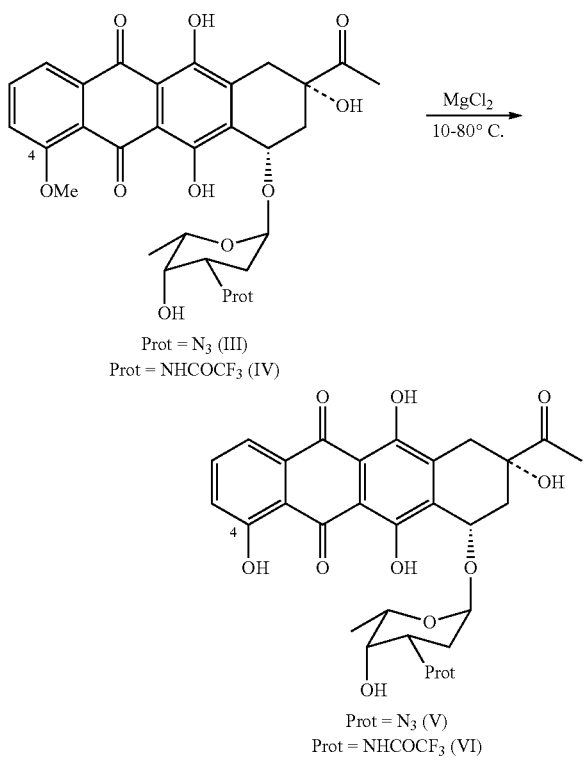

Prot = N₃ (V)
Prot = NHCOCF₃ (VI)

The term "Lewis acid", as used herein, denotes a molecular entity (and the corresponding chemical species) that is an electron-pair acceptor and therefore able to react with a Lewis base to form a Lewis adduct, by sharing the electron pair furnished by the Lewis base. Lewis acids and bases are commonly classified according to their hardness or softness. In this context, hard implies small and non-polarizable atoms, whereas soft indicates larger atoms that are more polarizable.

TABLE 1

Interaction of 3'-Prot-daunorubicin with different Lewis acids.

| No | Catalyst | Result |
|----|----------|--------|
| 1 | AlCl₃ | Aglycon (C7 bond cleavage) + resinification |
| 2 | BF₃ | Aglycon (C7 bond cleavage) |
| 3 | TiCl₄ | Aglycon (C7 bond cleavage) |
| 4 | MgCl₂ anhydrous | Demethylation of 4-OMe |
| 5 | MgCl₂*6H₂O | Reaction does not proceed |
| 6 | MgCl₂*4H₂O | Reaction does not proceed |
| 7 | MgCl₂*2H₂O | Reaction does not proceed |

Demethylation of the 4-MeO group of 3'-Prot-daunorubicin could be achieved by using a soft Lewis acid, MgCl₂ (anhydrous). No concomitant cleavage of the glycosidic linkage at carbon C7 was observed. In contrast, use of MgCl₂*6H₂O, MgCl₂*4H₂O and MgCl₂*2H₂O did not provide reasonable results. The use of harder Lewis acid species such as AlCl₃, BF₃, or TiCl₄ all resulted in undesirable cleavage of the glycosidic bond to yield the aglycone.

In some embodiments, the 4-demethylation reaction is performed by treating the 3'-Prot-daunorubicine having the chemical structure of formula (III) or (IV) with the soft Lewis acid MgCl₂ (anhydrous) at a reaction temperature in the range of 10-80° C. The reaction temperature depends on the activity of the Lewis acid used and it should provide maximal regioselectivity of the reaction: demethylation of the 4-OMe group without concomitant cleavage glycosidic linkage at carbon C7. Preferably, the reaction temperature is in the range of 40-60° C.

The 4-demethylation reaction can be performed in the presence of KI in an anhydrous solvent (resistant to Lewis acids) being selected from the group consisting of alkanes, cycloalkanes, haloalkanes, arenes, alkyl oxides, ethers, $C_4$-$C_6$ alcohols, and carbon disulfide. Solvents selected from haloalkanes and ethers are particularly preferred. The Lewis acid can be present in a 1-5 fold molar excess over 3'-Prot-daunorubicine (the latter is typically present in an amount of 1.5-3 moles).

In some specific embodiments, the product of the 4-demethylation reaction, a 4-demethyl-3'-Prot-daunorubicin having the chemical structure of formula (V) or (VI) is isolated by treatment of the reaction mixture with aqueous solutions of strong acids (such as inter alia oxalic acid, trifluoroacetic acid, sulfuric acid, and hydrochloric acid) at a pH of 2.5±1.0 and subsequent extraction by water-insoluble organic acids (in case of using water-soluble ethers). The 4-demethyl-3'-Prot-daunorubicine compounds (V, VI) are then isolated by evaporation of the organic phase in vacuum.

In various embodiments, the compound of formula (V) or formula (VI) can be converted to caminomycin directly by deprotection, such as is described below for deprotection of the 3'-protected 4-demethoxydaunorubicin derivatives. Accordingly, the invention provides a short and efficient method of preparation of caminomycin or salts thereof from daunorubicin or its salts.

In the preparation of 4-demethoxydaunorubicin, the demethylated 3'-Prot-daunorubicin compounds of formula (V) or (VI) is then sulfonated at the 4-OH group to provide the compounds of formula (VII) or (VIII) respectively by contacting with a trifluoromethanesulfonation reagent. For example, trifluoromethanesulfonation can be carried out by reacting the compound of formula (V) or (VI) with trifluoromethanesulfonic anhydride (Tf₂O). The reaction may be performed in pyridine in the presence of sterically hindered tertiary amines, such as inter alia N,N-diisoprolylethylamine, and catalytic amounts of N,N-dimethyl aminopyridine. The hydroxyl groups at carbons C6, C11 and C9 do not react under the experimental conditions used herein (cf. Example 4 below).

The reaction product of this synthesis step is a 4-O-trifluoromethanesulfonyl-3'-Prot-daunorubicin having the chemical structure of formula (VII) or (VIII).

The reaction is illustrated in the following scheme 5:

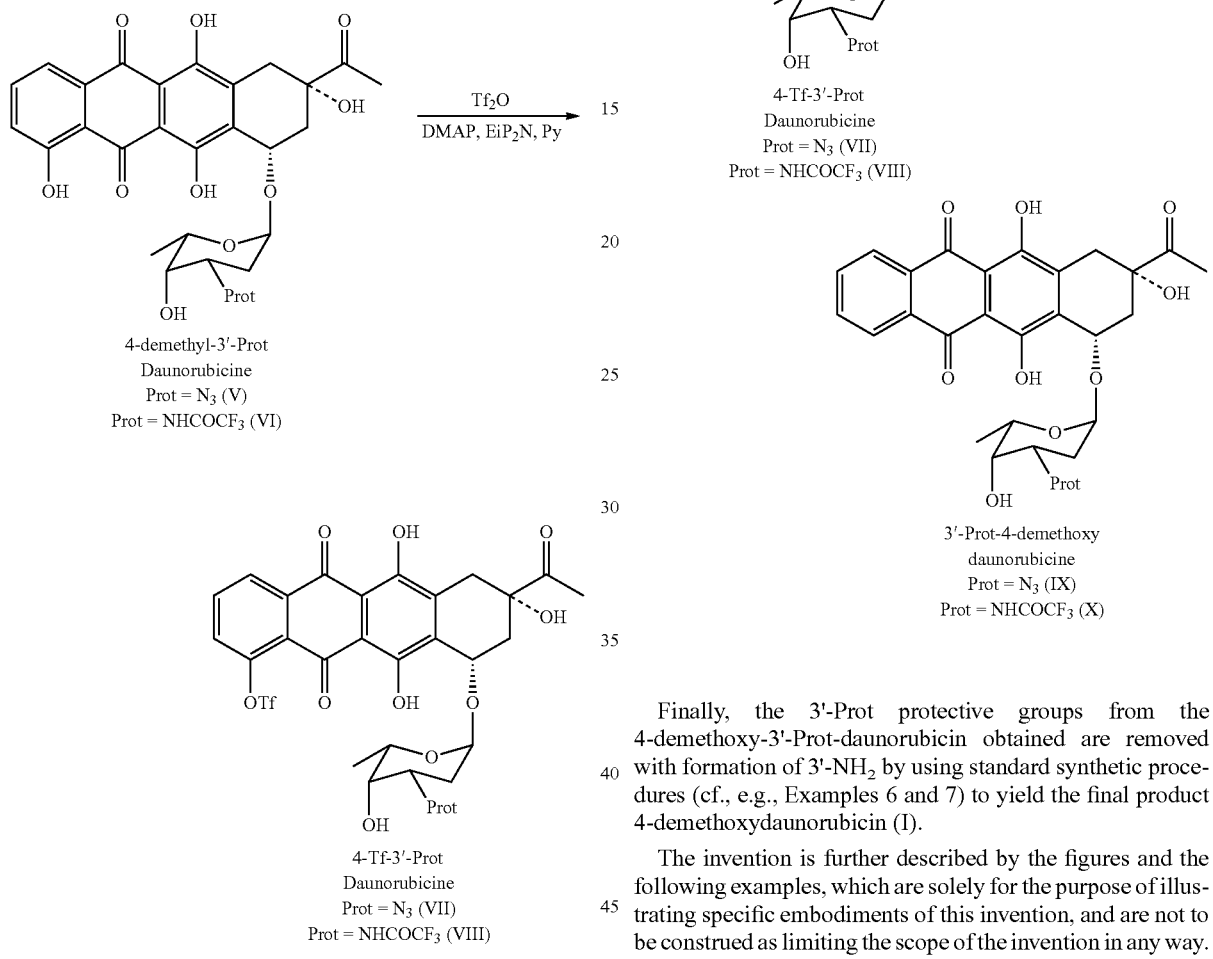

Subsequently, the 4-trifluoromethanesulfonate derivative of the 3'-protected 4-demethyldaunorubicin (VII, VIII) is reacted with a reducing agent selected from formic acid and salts of formic acid in the presence of catalytic amounts (molar ratios in the range from 1:1 to $1:10^4$, preferably from 1:20 to 1:100) of compounds having the general formula $PdL_nL'_m$; wherein Pd represents palladium, L and L' are independently selected from the group consisting of phosphites and phosphines; and n and m may independently vary from 0 to 4. Preferred phosphines to be employed herein include inter alia diphenylphosphino propane and 1,1'-bis(diphenylphosphino)ferrocene. Preferably, this step is performed at a reaction temperature in the range of 30-100° C. in a polar aprotic solvent, particularly in alkylamides in an inert atmosphere.

The reaction product of this synthesis step illustrated in the following scheme 6 is a 3'-Prot-4-demethoxydaunorubicine having the chemical structure of formula (IX) or (X).

Finally, the 3'-Prot protective groups from the 4-demethoxy-3'-Prot-daunorubicin obtained are removed with formation of 3'-$NH_2$ by using standard synthetic procedures (cf., e.g., Examples 6 and 7) to yield the final product 4-demethoxydaunorubicin (I).

The invention is further described by the figures and the following examples, which are solely for the purpose of illustrating specific embodiments of this invention, and are not to be construed as limiting the scope of the invention in any way.

EXAMPLES

Example 1

20 g of daunorubicin hydrochloride (II) were dissolved in 125 ml of MeOH. 7.5 g of $K_2CO_3$ were added to 20 ml of water, stirred vigorously for 1 minute and added to a solution of trifluoromethanesulfonyl azide ($TfN_3$) in dichloromethane. The mixture is stirred on a magnetic stirrer until the complete dissolution of the anthracycline starting compound. The reaction mixture is then added to 300 ml of water. The organic layer was removed, and the water phase was extracted by means of dichloromethane. The remaining dichloromethane is evaporated on a rotary evaporator.

About 20 g of 3'-$N_3$-daunorubicine (III) with the purity of >90% were obtained. Purity is sufficient for the further synthesis protocol.

Example 2

20 g of daunorubicine hydrochloride (II) were slurried in 400 ml of dichloromethane (DCM), cooled to 0° C. 28 ml of trifluoroacetic anhydride were added to 45 ml of DCM solution, while vigorously stirring for 1 hour. The mixture was kept at 0° C. for another 30 min, added to 750 ml of distilled water, and stirred. The organic layer was removed.

400 ml of saturated sodium bicarbonate solution were added to the organic layer and kept at room temperature while vigorously stirring for 15-25 hours in order to hydrolyse the 4'O-3'N-di-trifluoroacetyldaunomycine. After terminating the hydrolysis (HPLC control) the organic layer was separated and the solvent completely evaporated at reduced pressure.

After evaporation 20 g of N-trifluoroacetamidodaunorubicine (IV) were obtained having a purity of 93% (confirmed by HPLC). Purity is sufficient for the further synthesis protocol.

Example 3

20 g of 3'-Prot-daunorubicine (III, IV) were dissolved in 450 ml of tetrahydrofuran. 25 g of anhydrous magnesium chloride and 20 g of anhydrous potassium iodide were added in an environment excluding contact with atmospheric moisture. The mixture was kept at 40° C. for 1.5 hours, added to ice water and acidified to a pH of 2.5 by using trifluoroacetic acid. Then, the mixture was extracted with 2×150 ml of dichloromethane.

The organic layer was removed, dried using anhydrous $MgSO_4$, and the solvent was evaporated at reduced pressure. 15.8 g of 4-demethyl-3'-Prot-daunorubicine (V, VI) were obtained having a purity of >90% (confirmed by HPLC).

Example 4

The thoroughly dried 4-demethyl-3'-Prot-daunorubicine (V, VI) of Example 3 was dissolved in 800 ml of pyridine. 28 ml of diisopropylethylamine and 3.5 g of 4-dimethylaminopyridinium were added, and the mixture cooled to 0° C. 7.5 ml of freshly distilled trifluoromethanesulfonic acid anhydride were added, and the mixture kept for 1 hour at room temperature. Then, 650 ml of concentrated hydrochloric acid, 0.8 kg of ice and 800 ml of dichloromethane were added. The organic layer was rinsed twice using 500 ml of distilled water, separated and the dichloromethane removed at reduced pressure.

20 g of 4-O-trifluoromethanesulfonyl-3'-Prot-daunorubicin (VII, VIII) with a purity of 75-90% were obtained and used for the subsequent synthesis steps without further purification.

Example 5

The 4-O-trifluoromethanesulfonyl-3'-Prot-daunorubicine (VII, VIII) of Example 4 was dissolved in 500 ml of dimethyl formamide. 12 g of triethylamine formate and 350 mg of palladium acetate were added under stirring in an argon atmosphere. The mixture was heated to 50° C., 1.2 g of 1,1'-bis (diphenylphosphino)ferrocene were added, and the mixture was further heated for 8 hours.

The reaction mixture was added to water under vigorous stirring, before the 4-demethoxy-3'-Prot-daunorubicin was separated by filtering and purified by preparative chromatography. 9.5-11.5 g of 4-demethoxy-3'-Prot-daunorubicin (IX, X) with a purity of 96-98% were obtained.

Example 6

In case of the 3'-protecting group being $N_3$ (IX), the intermediate obtained was dissolved in 200 ml of tetrahydrofuran, and 14 g of triphenylphosphine were added. The solution was kept at room temperature to enable full conversion of 4-demethoxydaunorubicin azide. Then, 10 g of ammonia solution in methanol were added, and incubated until full conversion of the 3'-phosphine-imine of 4-demethoxydaunorubicine was obtained.

The reaction mixture was evaporated and the final reaction product purified by means of preparative chromatography. After repeated chromatographic purification and crystallization 8-8.5 g of 4-demethoxy-daunorubicine (I) with a purity of >99.5% were obtained (i.e. an overall yield of 40-42.5% based on the amount of starting material).

Example 7

In case of the 3'-protective group being $COCF_3$ (X), 9.5 g of 4-demethoxy-3'-trifluoroacetamido-daunorubicin were slurried in 300 ml of water at a temperature of 30° C. Then, 30 ml of 1.0 N NaOH solution were added under stirring. The mixture was incubated for 30 min, neutralized to a pH of 7.0 using a solution of hydrochloric acid.

The reaction mixture was evaporated and the final reaction product purified by means of preparative chromatography. Finally, 8.2-8.8 g of 4-demethoxydaunorubicine (I) with a purity of >99.5% were obtained (i.e. an overall yield of 41-44% based on the amount of starting material).

The present invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by embodiments and optional features, modifications and variations of the inventions embodied therein may be resorted to by those skilled in the art, and that such modifications and variations are considered to be within the scope of this invention.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A method for the production of 4-demethoxydaunorubicin or a salt thereof having the chemical structure of formula (I),

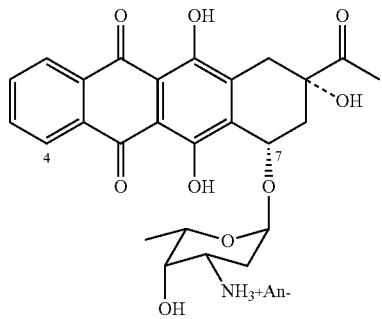

wherein An represents an anion, comprising:
(a) converting a daunorubicin hydrochloride salt having the chemical structure of formula (II)

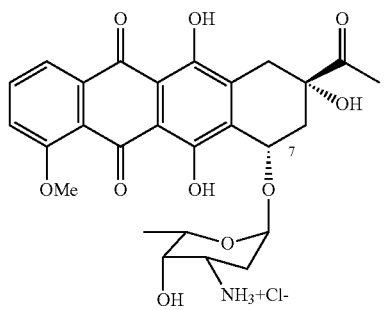

into a 3'-protected daunorubicin (3'-Prot-daunorubicin) being selected from the group consisting of the compounds having the chemical structures of formulas (III) and (IV), wherein conversion of the 3'-amino group salt to a 3'-azide by contacting with an azide-forming reagent results in formation of (III), and conversion of the 3'-amino group salt to a 3'-trifluoroacetmide by contacting with a trifluoroacetylating reagent results in formation of (IV);

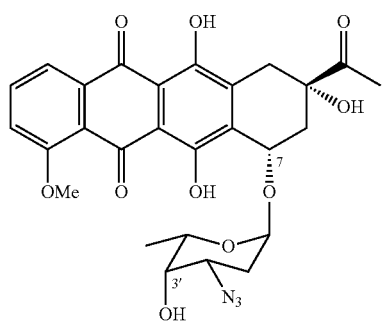

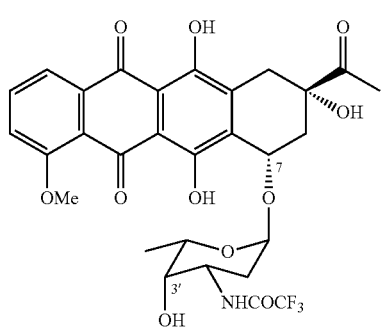

(b) demethylating the 3'-Prot-daunorubicin of formula (III) or (IV) by contacting with $MgCl_2$ (anhydrous) and in the presence of KI (anhydrous) in an anhydrous solvent to yield a 4-demethyl -3'-Prot-daunorubicin being selected from the group consisting of the compounds having the chemical structures of formulas (V) and (VI), respectively, wherein demethylation of (III) results in formation of (V), and demethylation of (IV) results in formation of (VI), wherein the reaction is performed at a reaction temperature in the range of 10-80° C., and in particular in the range of 40-60° C., and wherein the anhydrous solvent is selected from the group consisting of alkanes, cycloalkanes, halogenalkanes, arenes, alkyl oxides, ethers, $C_4$-$C_6$ alcohols, and carbon disulfide;

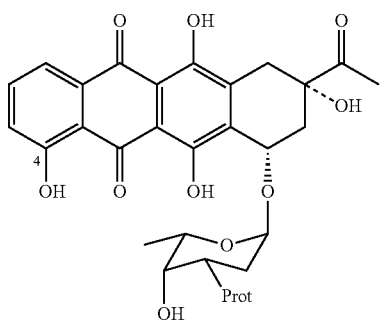

Prot = $N_3$ (V)
Prot = $NHCOCF_3$ (VI)

(c) trifluoromethanesulfonylating the 4-demethyl-3'-Prot-daunorubicin of formula (V) or (VI) by contacting with a trifluoromethanesulfonation reagent to yield a 4-O-trifluoromethanesulfonyl -3'-Prot-daunorubicin being selected from the group consisting of the compounds having the chemical structures of formulas (VII) and (VIII), respectively, wherein trifluoromethanesulfonylation of (V) results in formation of (VII), and trifluoromethanesulfonylation of (VI) results in formation of (VIII);

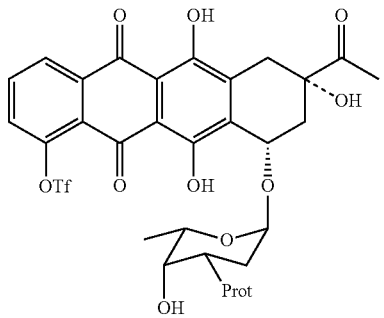

4-Tf-3'-Prot
Daunorubicine

Prot = $N_3$ (VII)
Prot = $NHCOCF_3$ (VIII)

(d) reducing the 4O-trifluoromethanesulfonyl-3'-Prot-daunorubicin of formula (VII) or (VIIII) by contacting with a reducing agent to yield a 4-demethoxy-3'-Prot-daunorubicin being selected from the group consisting of the compounds having the chemical structures of formulas (IX) and (X), respectively, wherein reduction of (VII) results in formation of (IX), and reduction of (VIII) results in formation of (X); and

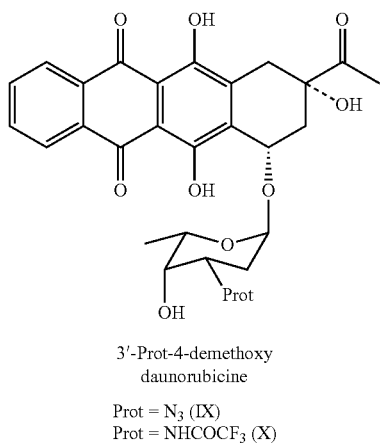

3'-Prot-4-demethoxy
daunorubicine

Prot = N₃ (IX)
Prot = NHCOCF₃ (X)

(e) removing the protective 3'-Prot group from the 4-demethoxy-3'-Prot-daunorubicin selected from the group consisting of the compound of formula (IX) and the compound of formula (X), wherein the compound of formula (IX) is contacted with an azide-reducing reagent, or the compound of formula (X) is contacted with an alkaline solution, with resulting formation of a 3'-amino group, to yield 4-demethoxy-daunorubicin and, optionally, contacting 4-demethoxydaunorubicin with an acid of formula H+An— to yield 4-demethoxy-daunorubicin salt of formula (I).

2. The method of claim 1, wherein step (a) is performed by reacting daunorubicin hydrochloride with a compound being selected from the group consisting of trifluoromethanesulfonyl azide and trifluoroacetic anhydride to provide a compound of formula (III) or a compound of formula (IV), respectively.

3. The method of claim 1, wherein step (c) is performed by reacting the 4-demethyl-3'-Prot-daunorubicin of formula (V) or (VI) with trifluoromethanesulfonic anhydride to provide the trifluoromethanesulfonated compounds of formula (VII) or (VIII), respectively, and wherein step (c) is preferably performed in pyridine in the presence of tertiary amines.

4. The method of claim 1, wherein step (d) is performed by reacting the 4-trifluoromethanesulfonyl-3'-Prot-daunorubicin of formula (VII) or (VIII) with a reducing agent in the presence of catalytic amounts of compounds having the general formula $PdL_nL'_m$, wherein L and L' are independently selected from the group consisting of phosphites and phosphines; and n and m may independently vary from 0 to 4; and wherein the reducing agent is selected from the group consisting of formic acid and salts of formic acid; to provide the compound of formula (IX) or formula (X), respectively.

5. The method of claim 4, wherein step (d) is performed at a reaction temperature in the range of 30-100° C. in a polar aprotic solvent.

6. The method of claim 1, wherein the azide-reducing reagent of step (e) comprises triphenylphosphine.

7. The method of claim 1, wherein the alkaline solution of step (e) comprises aqueous sodium hydroxide.

8. The method of claim 1, further comprising: isolating the 4-demethyl-3'-Prot-daunorubicin of formula (V) or (VI) obtained in step (b) by treatment with strong acids at a pH of 2.5±1.0 and subsequent extraction.

* * * * *

UNITED STATES PATENT AND TRADEMARK OFFICE
CERTIFICATE OF CORRECTION

PATENT NO.         : 8,846,882 B2                                          Page 1 of 1
APPLICATION NO.    : 13/097131
DATED              : September 30, 2014
INVENTOR(S)        : Zabudkin et al.

It is certified that error appears in the above-identified patent and that said Letters Patent is hereby corrected as shown below:

In the Claims

Column 17, line 18, Claim 1, delete "An" and insert --An⁻--, therefor

Column 18, line 2, Claim 1, delete "MgC1₂." and insert --MgCl₂--, therefor

Column 18, line 4, Claim 1, delete "4-demethyl -3-Prot-daunorubicin" and insert --4-demethyl-3-Prot-daunorubicin--, therefor Column 18, line 37-38, Claim 1, delete "4-O-trifluoromethanesulfonyl -3'-Prot-daunorubicin" and insert --4-O-trifluoromethanesulfonyl-3'-Prot-daunorubicin--, therefor Column 19, line 2, Claim 1, delete "4O" and insert --4-O--, therefor Column 19, line 2, Claim 1, delete "(VIIII)" and insert --(VIII)--, therefor Column 20, line 1, Claim 1, delete "H+An--"and insert --H⁺An⁻--, therefor Column 20, line 34, Claim 8, delete "4-demethyl -3-Prot-daunorubicin" and insert --4-demethyl-3-Prot-daunorubicin--, therefor Signed and Sealed this
Seventeenth Day of February, 2015

Michelle K. Lee
*Deputy Director of the United States Patent and Trademark Office*